US011707290B2

(12) United States Patent
Olsen et al.

(10) Patent No.: US 11,707,290 B2
(45) Date of Patent: Jul. 25, 2023

(54) STENT RETRIEVER WITH RADIOPAQUE MEMBERS

(71) Applicant: ACCUMEDICAL BEIJING LTD., Beijing (CN)

(72) Inventors: Daniel Olsen, Califon, NJ (US); Jin Park, Morris Plains, NJ (US)

(73) Assignee: ACCUMEDICAL BEIJING LTD., Beijing (CN)

( * ) Notice: Subject to any disclaimer, the term of this patent is extended or adjusted under 35 U.S.C. 154(b) by 117 days.

(21) Appl. No.: 17/132,405

(22) Filed: Dec. 23, 2020

(65) Prior Publication Data
US 2022/0192688 A1 Jun. 23, 2022

(51) Int. Cl.
*A61B 17/221* (2006.01)
*A61F 2/01* (2006.01)
*A61B 90/00* (2016.01)
*A61B 17/00* (2006.01)

(52) U.S. Cl.
CPC ........... *A61B 17/221* (2013.01); *A61F 2/013* (2013.01); *A61B 2017/00526* (2013.01); *A61B 2017/00867* (2013.01); *A61B 2017/2212* (2013.01); *A61B 2090/3966* (2016.02)

(58) Field of Classification Search
CPC ........ A61B 17/221; A61B 2017/00526; A61B 2017/00867; A61B 2017/2212; A61B 2017/2215; A61B 2017/2217; A61B 2090/3966; A61F 2/013; A61F 2/014; A61F 2002/016; A61F 2002/018
USPC ....................................................... 606/159
See application file for complete search history.

(56) References Cited

U.S. PATENT DOCUMENTS

| 8,632,584 | B2 | 1/2014 | Henkes |
| 10,842,498 | B2 | 11/2020 | Vale |
| 2007/0135820 | A1* | 6/2007 | Que ................ A61B 17/221 606/127 |
| 2013/0030460 | A1* | 1/2013 | Marks ............. A61B 17/221 606/200 |
| 2014/0121672 | A1* | 5/2014 | Folk ................. A61F 2/013 606/127 |
| 2014/0277079 | A1* | 9/2014 | Vale ................ A61B 17/221 606/200 |
| 2017/0079766 | A1* | 3/2017 | Wang ............... A61B 17/22 |
| 2021/0378692 | A1* | 12/2021 | Xiang .............. A61B 17/221 |

OTHER PUBLICATIONS

Wire Definition Meaning Meriam Webster, https://www.merriam-webster.com/dictionary/wire, accessed Jun. 14, 2022, Copyright 2022 Merriam-Webster, Incorporated (Year: 2022).*

* cited by examiner

*Primary Examiner* — Kankindi Rwego
(74) *Attorney, Agent, or Firm* — Master Key IP, LLP; Justin G. Sanders

(57) ABSTRACT

The present invention pertains to a thrombectomy device comprising a cylindrical proximal portion and one or more radiopaque segments. The cylindrical proximal portion forms a stent frame having an outer lattice network of an outer plurality of interconnecting segments. The outer plurality of interconnecting segments are configured to exert a radial force against an inner wall of a blood vessel. The radiopaque segment is formed from a plurality of radiopaque wires extending from the outer stent frame to a central axis of the thrombectomy device along a length of the stent frame. The radiopaque segment converges to a tip along with the central axis.

15 Claims, 8 Drawing Sheets

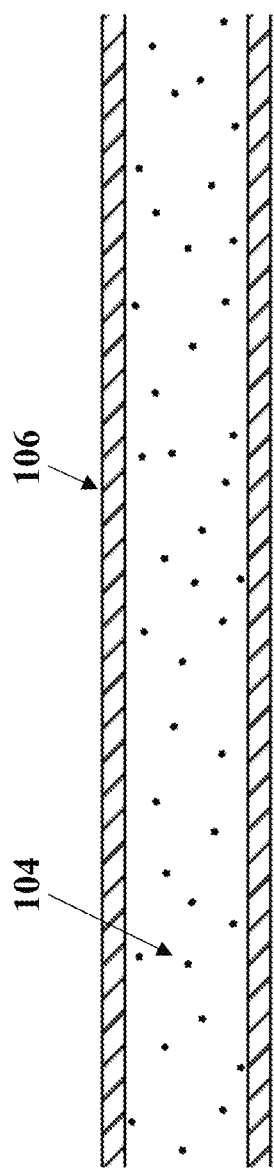

STENT RETRIEVER WITH RADIOPAQUE MEMBERS

TECHNICAL FIELD

The present invention is generally related to the field of catheter-based removal of unwanted matter from cerebral vascular structures and more particularly to stent retrievers having additional radiopaque segments on the interior lumen of the device to improve visualization in vivo and thrombus retention and removal from cerebral vascular structures.

BACKGROUND

Stent retriever technology has historically been used to remove thrombus (i.e., blood clot) from the neurovasculature (i.e., blood vessels in the brain) in a procedure known as neurothrombectomy for the treatment of strokes. The thrombus causes occlusion of the blood vessel, restricting blood flow and significantly reducing oxygen and nutrient delivery to surrounding tissue. As the thrombus persists, tissue distal to the thrombus experiences necrosis (i.e., cellular death), which can ultimately lead to brain damage or death, amongst other negative conditions. Stent retriever technology is intended to capture the thrombus and remove it from the effected blood vessel, thereby returning normal flow to the vessel and preventing further necrosis of the tissue.

Conventional methods require expanding a metal device into the thrombus to secure itself, and then removing the device and the thrombus in tandem. In a clinical setting, the visibility, otherwise known as the radiopacity of the device, is of critical importance, as it ensures that the clinician deploys the device in the correct location to capture the thrombus. Improper visualization can lead to increased surgical time and vessel damage as multiple attempts must be made to capture the thrombus, or, in a more severe situation, the thrombus may not be fully captured and, therefore, fragmented. In that scenario the fragmented thrombus may continue distal through the vessel until another thrombus occurs further downstream, further risking patient safety.

Conventional stent devices are typically manufactured from a nitinol alloy, which is not inherently radiopaque to an acceptable degree for this application. Known methods of improving visibility include coating the nitinol in a layer of tantalum and/or adding radiopaque marker bands throughout the device. While these methods improve visibility of the device in vivo, neither method improves the functionality of the device. Moreover, both of these methods increase the manufacturing time and complexity, while introducing potential additional failure modes to the device design.

A thrombectomy device has been disclosed in prior art 1, reference patent number U.S. Pat. No. 8,632,584. The prior art 1 discloses a longitudinally open tube with interconnected strings or filaments forming a mesh structure designed to capture thrombus in small-lumen intra-cranial vessels. However, the device disclosed in prior art 1 lacks any additional measures to improve radiopacity, or any additional measures to improve thrombus capture in vivo, creating a potentially difficult surgical environment.

A thrombectomy device has been disclosed in prior art 2, reference patent number U.S. Pat. No. 10,842,498. The prior art 2 discloses a longitudinal tube with interconnected segments forming a mesh structure similar to that disclosed in prior art 1. The prior art 2 discloses a thrombectomy device having additional protruding segments from the mesh structure to increase the likelihood of thrombus proliferation and capture. The bulk of the main body of the mesh is kept on the interior of the device, while the protruding segments extend outward toward the vessel, creating an opportunity for fragmentation of the thrombus resulting in secondary emboli. While the device, in theory, may add additional measures to improve thrombus capture, it is limited in that the entire device cannot open to the full diameter.

Therefore, there is a need for a thrombectomy device that provides superior thrombus integration for removal of thrombus from the vasculature and incorporates the radiopaque elements of the device in a way that is beneficial to the overall function of the device without sacrificing other functional components.

SUMMARY

At least the above-discussed need is addressed and technical solutions are achieved in the art by various embodiments of the present invention. Some embodiments of the present invention pertain to a thrombectomy device comprising a cylindrical proximal portion forming a stent frame having an outer lattice network of an outer plurality of interconnecting segments, the outer plurality of interconnecting segments being configured to exert a radial force against an inner wall of a blood vessel and a plurality of radiopaque wires forming a radiopaque segment, the plurality of radiopaque wires extending from the outer stent frame to a central axis of the thrombectomy device along a length of the stent frame, the radiopaque segment converging to a tip along with the central axis.

In some embodiments of the invention, the radiopaque segment is formed at a distal end of the stent frame. In some embodiments of the invention, the radiopaque segment has a convex shape extending along the length of the stent frame.

In some embodiments of the invention, the thrombectomy device includes a plurality of radiopaque segments. At least one radiopaque segment of the plurality of radiopaque segments is formed at a distal end of the stent frame, and the remaining radiopaque segments of the plurality of radiopaque segments are uniformly distributed along the length of the stent frame.

In some embodiments of the invention, the outer plurality of interconnecting segments is arranged to include openings when the stent frame of the thrombectomy device is deployed in an open position, and the radiopaque segment is arranged to include openings when the device is deployed in an open position. In some embodiments of the invention, the outer plurality of interconnecting segments is arranged to be fully connected without any openings when the stent frame of the thrombectomy device is deployed in a closed position, and the radiopaque segment is arranged to be fully connected without any openings when the thrombectomy device is deployed in a closed position.

In some embodiments of the invention, the openings in the outer stent frame have a smaller cross-section than the openings in the radiopaque segment.

In some embodiments of the invention, the outer stent frame is formed by laser cutting nitinol tubing and the radiopaque segment is formed from radiopaque wire. In some embodiments of the invention, the radiopaque segment reinforces the outer stent frame to improve thrombus retention and retrieval and radial strength.

In some embodiments of the invention, the stent frame is configured to capture a thrombus in the blood vessel, and the radiopaque segment is configured to increase visibility under radiographic imaging and increase retention of the thrombus during deployment and retrieval of the device.

In some embodiments of the invention, the radiopaque segment is formed from a plurality of radiopaque wires extending from the outer stent frame to a central axis of the thrombectomy device along a length of the stent frame to improve device radial strength, thrombus retention, and enhance visibility in vivo.

In some embodiments of the invention, the radiopaque segment is attached to the stent frame using radiopaque material by one of a soldering, welding, or brazing process.

In some embodiments of the invention, the plurality of radiopaque wires forming the radiopaque segment are superelastic.

In some embodiments of the invention, the radiopaque segments are formed of nitinol tubing with a radiopaque core (e.g. platinum) forming a solid radiopaque wire. In some embodiments of the invention, a plurality of multiple radiopaque wires coalesce into a singular point, where they are wound and bonded to form a tip. In this configuration, each radiopaque wire may attach to the outer stent frame to form the radiopaque segment. Alternatively, the radiopaque segment may be formed from a singular wire that is split and attached to multiple points on the outer stent frame.

In some embodiments of the invention, the tip formed by the radiopaque segment has supplemental radiopaque attributes to further enhance visibility in vivo.

In some embodiments of the invention, the thrombectomy device further includes a microcatheter designed to deliver and retrieve the thrombectomy device from the blood vessel in a closed position.

In some embodiments of the invention, the outer plurality of interconnecting segments is arranged to be fully connected without any openings when the stent frame of the thrombectomy device is deployed in a closed position, and the radiopaque segment is arranged to be fully connected without any openings when the device is deployed in a closed position.

In some embodiments of the invention, the distal end of the device tapers to a singular point where all remaining interconnecting segments are integrated.

In some embodiments of the invention, the outer stent frame is nitinol tubing laser cut to form the outer stent frame.

In some embodiments of the invention, the openings formed in the radiopaque segment are sized such that they increase contact surface area with the thrombus, further improving thrombus integration and capture during delivery and retraction of the device.

In some embodiments of the invention, the outer stent frame is configured to capture a thrombus in the blood vessel, and the inner stent frame is configured to further prevent thrombus migration and aid in capture of the thrombus in the blood vessel.

These and other embodiments of the invention are discussed in detail below.

BRIEF DESCRIPTION OF THE DRAWINGS

It is to be understood that the attached drawings are for purposes of illustrating aspects of various embodiments and may include elements that are not to scale. It is noted that like reference characters in different figures refer to the same objects.

FIG. 8 depicts a representative image of the blood vessel from FIG. 4 following removal of the thrombectomy device and the thrombus after completion of the treatment process, according to an embodiment of the invention.

DETAILED DESCRIPTION

Figure 1:
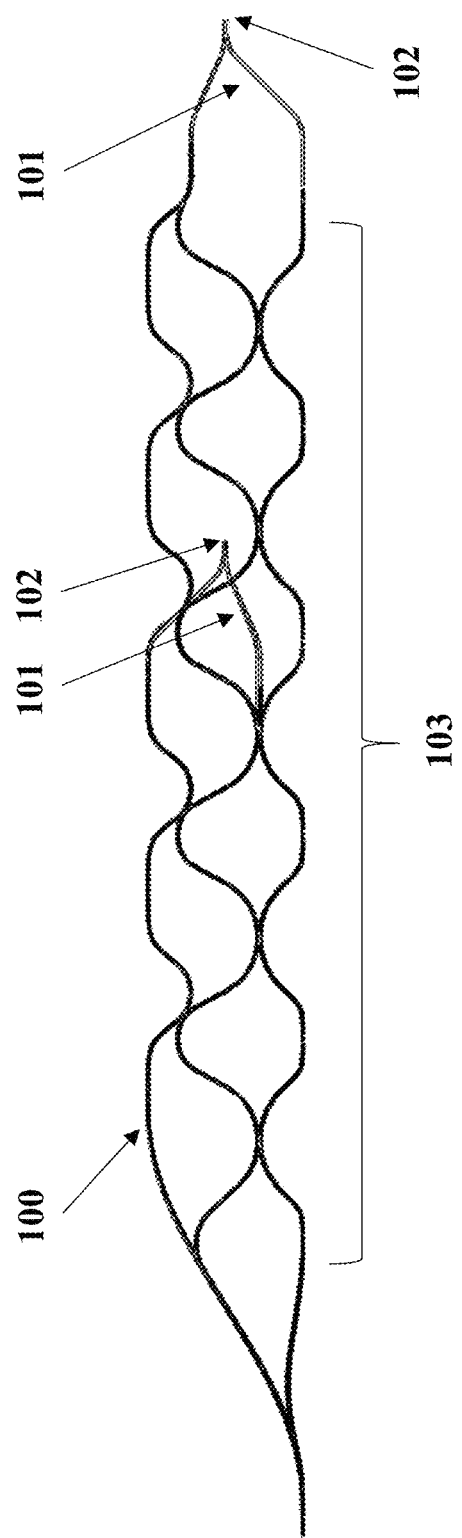
FIG. 1 depicts a side view of a thrombectomy device, according to an embodiment of the invention.

In the descriptions herein, certain specific details are set forth in order to provide a thorough understanding of various embodiments of the invention. However, one skilled in the art will understand that the invention may be practiced at a more general level without one or more of these details. In other instances, well-known structures have not been shown or described in detail to avoid unnecessarily obscuring descriptions of various embodiments of the invention.

Any reference throughout this specification to "one embodiment", "an embodiment", "an example embodiment", "an illustrated embodiment", "a particular embodiment", and the like means that a particular feature, structure or characteristic described in connection with the embodiment is included in at least one embodiment. Thus, any appearance of the phrase "in one embodiment", "in an embodiment", "in an example embodiment", "in this illustrated embodiment", "in this particular embodiment", or the like in this specification is not necessarily all referring to one embodiment or a same embodiment. Furthermore, the particular features, structures or characteristics of different embodiments may be combined in any suitable manner to form one or more other embodiments.

Unless otherwise explicitly noted or required by context, the word "or" is used in this disclosure in a non-exclusive sense. In addition, unless otherwise explicitly noted or required by context, the word "set" is intended to mean one or more. For example, the phrase, "a set of objects" means one or more of the objects.

In the following description, the phrase "at least" is or may be used herein at times merely to emphasize the possibility that other elements may exist beside those explicitly listed. However, unless otherwise explicitly noted (such as by the use of the term "only") or required by context, non-usage herein of the phrase "at least" nonetheless includes the possibility that other elements may exist besides those explicitly listed. For example, the phrase, 'including at least A' includes A as well as the possibility of one or more other additional elements besides A. In the same manner, the phrase, 'including A' includes A, as well as the possibility of one or more other additional elements besides A. However, the phrase, 'including only A' includes only A. Similarly, the phrase 'configured at least to A' includes a configuration to perform A, as well as the possibility of one or more other additional actions besides A. In the same manner, the phrase 'configured to A' includes a configuration to perform A, as well as the possibility of one or more other additional actions besides A. However, the phrase, 'configured only to A' means a configuration to perform only A.

The word "device", the word "machine", the word "system", and the phrase "device system" all are intended to include one or more physical devices or sub-devices (e.g., pieces of equipment) that interact to perform one or more functions, regardless of whether such devices or sub-devices are located within a same housing or different housings. However, it may be explicitly specified according to various embodiments that a device or machine or device system resides entirely within a same housing to exclude embodiments where the respective device, machine, system, or device system resides across different housings. The word "device" may equivalently be referred to as a "device system" in some embodiments.

Figure 2:
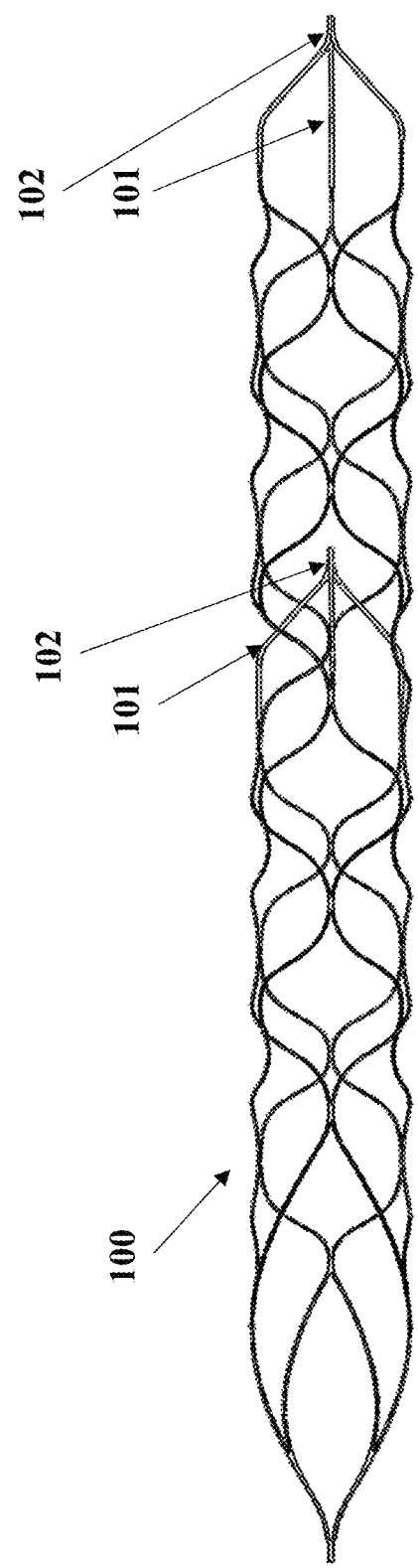
FIG. 2 depicts a side view of another thrombectomy device, according to an embodiment of the invention.

FIGS. 1-2 shows a thrombectomy device according to some embodiments of the present invention. The thrombectomy device includes a stent retriever frame 100 having two radiopaque segments 101 which terminate into tips 102. In some embodiments, the stent retriever frame 100 is formed from laser cut nitinol tubing while the radiopaque segments 101 are comprised of a plurality of nitinol wires with a radiopaque core (e.g. platinum). In some embodiments, the stent retriever frame 100 is formed from a lattice network of either non-rigid or rigid interconnected metallic segments designed to open to the vessel wall with a radial force significant enough to penetrate a blood clot but not damage the surrounding blood vessel. In some embodiments of the invention, the stent retriever frame 100 is open such that the metallic segments are not fully connected in the radial direction to facilitate integration into the thrombus. In some embodiments of the invention, the stent retriever frame 100 is closed such that the metallic segments are fully connected in the radial direction to increase device stability. In some embodiments of the invention, as shown in FIG. 1, the stent retriever frame 100 may be manufactured to various lengths 103 to accommodate different anatomical needs. In some embodiments of the invention, the lattice network of the stent retriever frame 100 may be manufactured to larger or smaller diameters to accommodate different anatomical needs. In some embodiments of the invention, the number of radiopaque segments 101 may be increased or decreased to align with the various lengths 103 of the stent retriever frame 100.

In some embodiments of the invention, the stent retriever frame 100 is manufactured using laser cutting of nitinol tubing. Laser cut tubing improves the manufacturability (e.g. speed, ease) compared to wire braiding. Additionally, laser cut tubing reduces the overall thickness of the device compared to wire braiding, which in turn reduces the overall device profile. A reduction in device profile corresponds with decreased difficulty in crossing the target thrombus and decreased difficulty in retraction upon clot retrieval, as well as improving the potential target locations in the vasculature.

Figure 3:
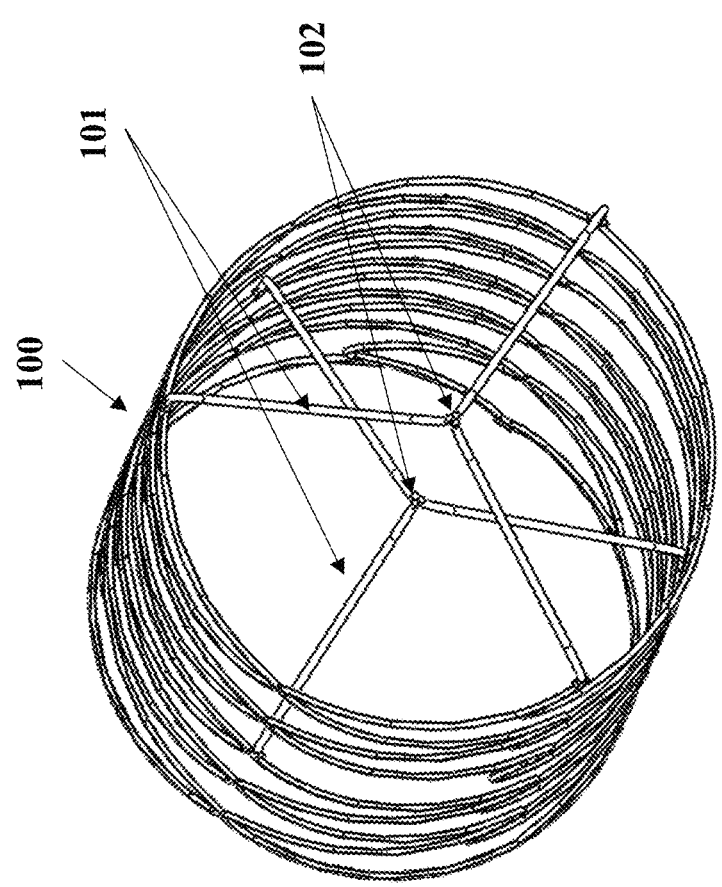
FIG. 3 depicts an end view of a distal end of a thrombectomy device, according to an embodiment of the invention.

In some embodiments of the invention, the radiopaque segments 101 act as a secondary stent retriever frame designed to further entrap a thrombus and prevent distal movement of the thrombus during deployment and retraction. FIG. 3 shows the device in the deployed position, with the radiopaque segments 101 extending inside of the outer stent retriever frame 100, creating an interior lattice network normal to the lattice network of the stent retriever frame 100. In some embodiments of the invention, the radiopaque segment 101 is convex in shape. The radiopaque segment 101 is designed such that it reinforces the outer stent frame 100 to improve radial strength. Enhancement of radial strength without thickening of the outer stent frame 100 may improve the crimped stent profile, further improving device deliverability and ease of use. In some embodiments of the invention, the radiopaque segment 101 is designed such that it will further increase the contact surface area of the thrombectomy device with the thrombus, giving multiple interior points of attachment to prevent distal movement of the thrombus during the procedure. In some embodiments of the invention, the radiopaque segment 101 is designed such that the segments act as radiopaque markers to improve procedural visibility in vivo.

In some embodiments of the invention, the radiopaque segments 101 are constructed of a plurality of radiopaque superelastic wires, which are attached to multiple locations on the outer stent retriever frame 100. The superelastic wires may be attached to the outer stent retriever frame 100 using a welding, soldering, or brazing process. In some embodiments of the invention, radiopaque material may be used to solder or attach the superelastic wires to the outer stent retriever frame 100.

Incorporation of the radiopaque superelastic wire allows the device to be superelastic, visualized in vivo while simultaneously acting as a functional component of the device, contrary to current visualization techniques that have limited to no functional use other than radiopacity. Integration of the radiopaque segment 101 in this way provides the benefit of radiopacity while not hindering the device with more difficult manufacturing techniques or increasing the overall crimped profile of the device.

In some embodiments of the invention, the number of radiopaque segments 101 may be increased or decreased to further improve the overall crimped profile or radiopaque properties of the device. There must be a minimum of one (1) radiopaque segment 101 on the thrombectomy device at the distal end. In some embodiments of the invention, any subsequent radiopaque segments 101 are equally spaced (uniformly distributed) throughout the length of the device 103. In some embodiments of the invention, each radiopaque segment 101 converges to a solid tip 102.

In some embodiments of the invention, the radiopaque segments 101 may be formed from a single radiopaque superelastic wire such that the tip 102 is a single solid wire and the plurality of radiopaque wires are split from the single original wire to attach to the outer stent frame 100 at multiple locations.

In some embodiments of the invention, the radiopaque segments 101 may be formed from a plurality of individual radiopaque wires that are each attached to the outer stent frame 100 and extend from the outer stent frame 100 to a central axis of the thrombectomy device along a length of the stent frame 103, converging to a tip 102 aligned with the central axis of the thrombectomy device. In some embodiments of the invention, the tip 102 is formed through coiling and bonding the plurality of individual radiopaque wires to form a complete radiopaque segment. In some embodiments of the invention, the tip 102 may incorporate additional radiopaque material (e.g. tantalum) to further enhance the thrombectomy device radiopacity.

As shown in FIGS. 1-3, in some embodiments of the invention, the lattice network of the stent retriever frame 100 and radiopaque segments 101 are rigid in that the lattice network is fully interconnected and funnels to a singular point, the distal tip 102. In some embodiments of the invention, the lattice network of the radiopaque segments 101 has a window (opening) size (distance between metallic segments) larger than the window (opening) size of the lattice network of the stent retriever frame 100 to ensure that the device may be deployed to it's intended diameter without unnecessary additional resistance.

In some embodiments of the invention, each window (opening) of the lattice network of the thrombectomy device 100 has a cross sectional area preferably between 0.5 mm2 and 2 mm2. In some embodiments of the invention, the radiopaque segment 101 has a convex shape to increase the contact surface area to enhance capture and retrieval of the thrombus and to increase the cross sectional area visible during radiographic imaging.

Figure 4:
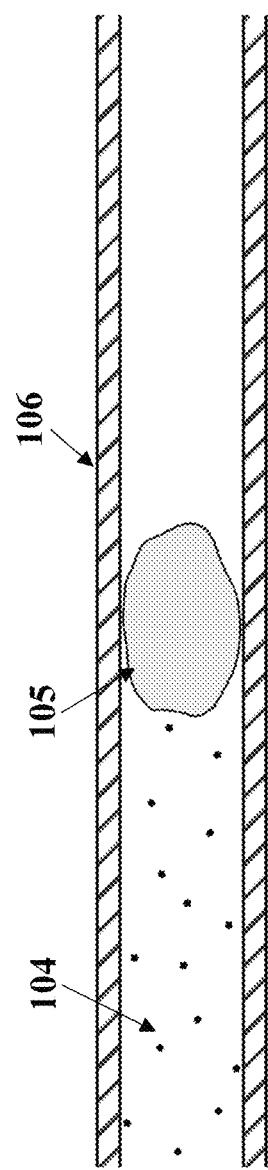
FIG. 4 depicts a representative image of a blood vessel obstructed by a thrombus, preventing blood flow to the distal end of the blood vessel, according to an embodiment of the invention.

FIGS. 4-8 show cross sectional views of a blood vessel during a treatment process using the thrombectomy device. FIG. 4 depicts a representative image of a blood vessel 106 obstructed by a thrombus 105, preventing blood flow 104 to the distal end of the blood vessel, according to an embodiment of the invention.

Figure 5:
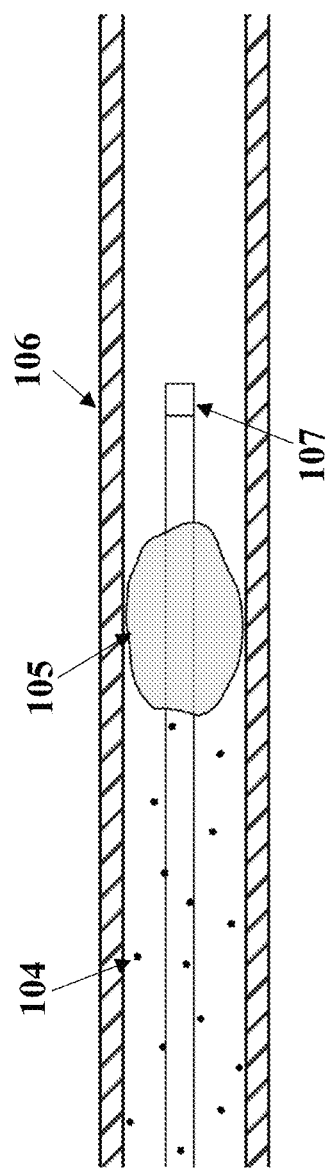
FIG. 5 depicts the obstructed blood vessel from FIG. 4 during the first step of a treatment process in which a microcatheter is inserted into the proximal end of the thrombus until it exits beyond the distal end of the thrombus according to an embodiment of the invention.
Figure 6:
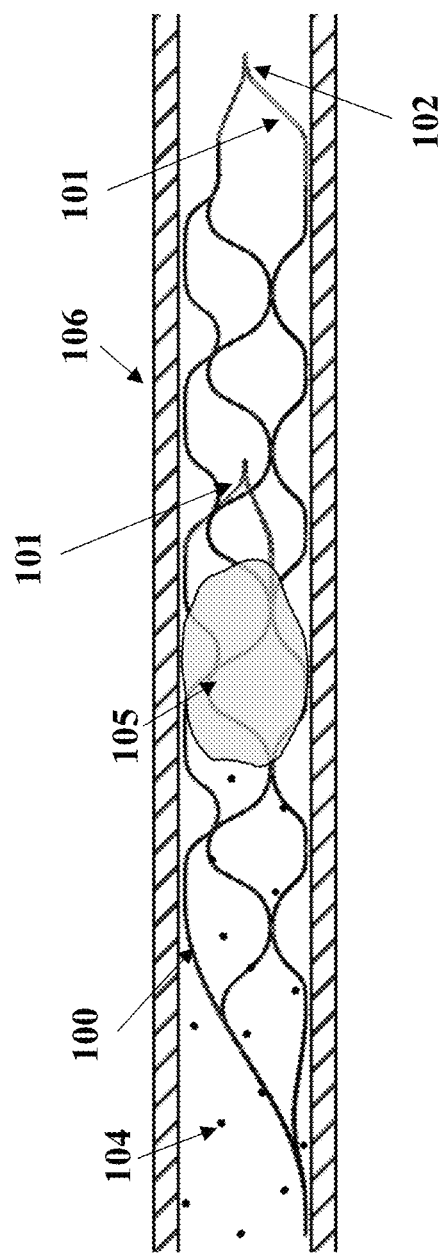
FIG. 6 depicts the obstructed blood vessel from FIG. 4 during the second step of the treatment process in which the thrombectomy device is advanced through the microcatheter and positioned across the thrombus and surrounding areas, according to an embodiment of the invention.

In some embodiments of the invention, the thrombectomy device is designed to treat a thrombus 105 in a blood vessel 106 where the thrombus 105 has impeded blood flow 104 to the distal end of the blood vessel 106. As shown in FIG. 5, in a first step of the treatment process, a microcatheter 107 is inserted into the effected blood vessel 106 distally through the thrombus 105. FIG. 6 shows the blood vessel 106 during a second step of the treatment process. In some embodiments of the invention, the thrombectomy device is advanced through the microcatheter 107 such that the stent frame 100 is both proximal and distal to the thrombus 105 simultaneously, and the distal radiopaque member 101 and distal tip 102 are distal to the thrombus 105.

Figure 7:
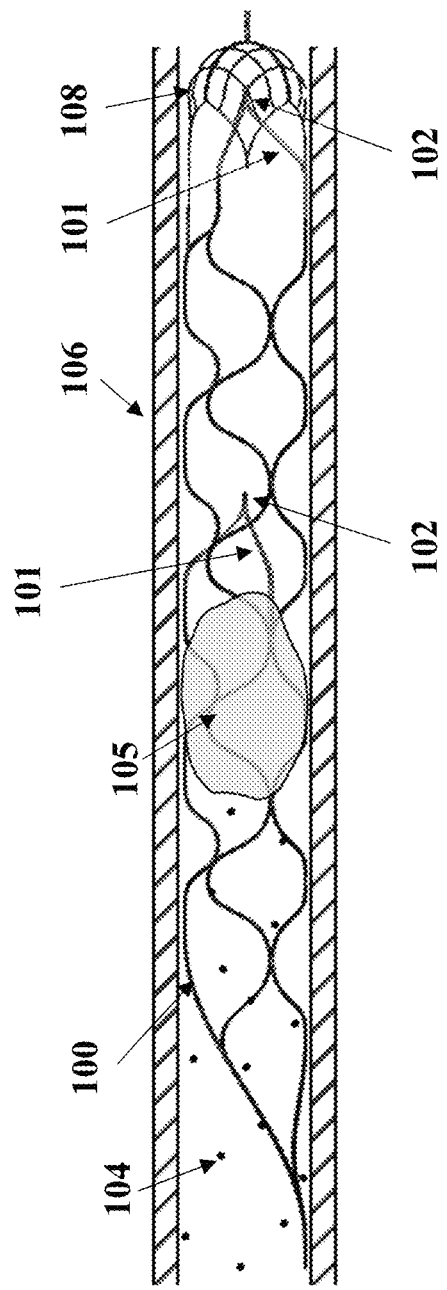
FIG. 7 depicts the obstructed blood vessel during the second step of the treatment process from FIG. 6 with an embolic protection device on the distal end of the thrombectomy device.

In some embodiments of the invention as shown in FIG. 7 the thrombectomy device may include an embolic protection device 108 on the distal end to reduce the risk and impact of secondary emboli.

In some embodiments of the invention, the thrombectomy device is designed such that it is self-expanding upon removal of a delivery sheath (microcatheter 107). The stent retriever frame 100 is designed to open up to a full vessel diameter, with different embodiments of the thrombectomy device being capable of expanding to a varying array of diameters and lengths to suit patient needs. The radiopaque segments 101 are designed to open up to a diameter varying between the maximum diameter obtained by the stent retriever frame 100 and the initial starting crimped diameter. In some embodiments of the invention, the stent retriever frame 100 exerts sufficient radial force to penetrate and integrate into a thrombus 105 without damaging the vessel wall 106.

In some embodiments of the invention, after self-expansion and integration into the thrombus 105, the thrombectomy device may be retracted into the microcatheter 107, refolding into its original compressed configuration with the thrombus 105 incorporated into the structure. As shown in FIG. 8, following removal of the device through the microcatheter 107, blood flow 104 is restored to the vessel 106 allowing for the delivery of critical nutrients to areas distal to treatment site. In some embodiments of the invention, the thrombectomy device is attached to a push wire used to advance the thrombectomy device to the target location through a microcatheter 107.

It should be understood that the invention is not limited to the embodiments discussed above, which are provided for purposes of illustration only. Subsets or combinations of various embodiments described above provide further embodiments of the invention.

These and other changes can be made to the invention in light of the above-detailed description and still fall within the scope of the present invention. In general, in the following claims, the terms used should not be construed to limit the invention to the specific embodiments disclosed in the specification. Accordingly, the invention is not limited by the disclosure, but instead its scope is to be determined entirely by the following claims.

The invention claimed is:

1. A thrombectomy device comprising:
    a cylindrical proximal portion forming a stent frame having an outer lattice network of an outer plurality of interconnecting segments with no elongate central member extending longitudinally along a central axis of the stent frame, the outer plurality of interconnecting segments being configured to exert a radial force against an inner wall of a blood vessel; and
    an at least one radiopaque segment comprising three radiopaque wires engaged with the stent frame in a circumferentially spaced apart arrangement, the three radiopaque wires of the at least one radiopaque segment radially extending inwardly from the stent frame and converging to form a singular, free-standing radiopaque tip positioned substantially on the central axis of the stent frame.

2. The thrombectomy device according to claim 1, wherein at least one of the at least one radiopaque segment is formed at a distal end of the stent frame.

3. The thrombectomy device according to claim 1, further comprising a plurality of radiopaque segments,
    wherein at least one radiopaque segment of the plurality of radiopaque segments is formed at a distal end of the stent frame, and
    wherein the remaining radiopaque segments of the plurality of radiopaque segments are uniformly distributed along a length of the stent frame.

4. The thrombectomy device according to claim 1, wherein the at least one radiopaque segment has a convex shape extending along a length of the stent frame.

5. The thrombectomy device according to claim 1, wherein the outer plurality of interconnecting segments is arranged to include openings when the stent frame of the thrombectomy device is deployed in an open position, and wherein the at least one radiopaque segment is arranged to include openings when the thrombectomy device is deployed in the open position.

6. The thrombectomy device according to claim 5, wherein the openings in the outer plurality of interconnecting segments have a smaller cross-section than the openings in the at least one radiopaque segment.

7. The thrombectomy device according to claim 1, wherein the stent frame is formed by laser cutting nitinol tubing.

8. The thrombectomy device according to claim 1, wherein the at least one radiopaque segment reinforces the stent frame to improve thrombus retention and retrieval and radial strength.

9. The thrombectomy device according to claim 1, further comprising a microcatheter designed to deliver and retrieve the thrombectomy device from the blood vessel in a closed position.

10. The thrombectomy device according to claim 1, wherein the outer plurality of interconnecting segments is arranged to be fully connected without any openings when the stent frame of the thrombectomy device is deployed in a closed position, and wherein the at least one radiopaque segment is arranged to be fully connected without any openings when the thrombectomy device is deployed in the closed position.

11. The thrombectomy device according to claim 1,
wherein the stent frame is configured to capture a thrombus in the blood vessel, and
wherein the at least one radiopaque segment is configured to increase visibility under radiographic imaging and increase retention of the thrombus during deployment and retrieval of the device.

12. The thrombectomy device according to claim 1, further comprising an embolic protection device connected to a distal end of the stent frame.

13. The thrombectomy device according to claim 1, wherein each of the radiopaque wires of the at least one radiopaque segment is attached to the stent frame using radiopaque material by one of a soldering, welding, or brazing process.

14. A thrombectomy device comprising:
a cylindrical proximal portion forming a stent frame having an outer lattice network of an outer plurality of interconnecting segments with no elongate central member extending longitudinally along a central axis of the stent frame, the outer plurality of interconnecting segments being configured to exert a radial force against an inner wall of a blood vessel; and
a plurality of longitudinally spaced apart radiopaque segments, each of the plurality of longitudinally spaced apart radiopaque segments comprising;
three or more radiopaque wires engaged with the stent frame in a circumferentially spaced apart arrangement; and
the three or more radiopaque wires of each of said plurality of longitudinally spaced apart radiopaque segments radially extending inwardly from the stent frame and converging to form a singular, free-standing radiopaque tip positioned substantially on the central axis of the stent frame.

15. A thrombectomy device comprising:
a cylindrical proximal portion forming a stent frame having an outer lattice network of an outer plurality of interconnecting segments with no elongate central member extending longitudinally along a central axis of the stent frame, the outer plurality of interconnecting segments being configured to exert a radial force against an inner wall of a blood vessel; and
an at least one radiopaque segment comprising three or more radiopaque wires engaged with the stent frame in a circumferentially spaced apart arrangement, the three or more radiopaque wires of the at least one radiopaque segment radially extending inwardly from the stent frame and converging to form a singular, free-standing radiopaque tip positioned substantially on the central axis of the stent frame.

* * * * *